(12) United States Patent
Cheng et al.

(10) Patent No.: US 11,931,151 B2
(45) Date of Patent: Mar. 19, 2024

(54) AUTOMATED URINARY OUTPUT MEASURING SYSTEM

(71) Applicant: C. R. Bard, Inc., Franklin Lakes, NJ (US)

(72) Inventors: Jason Jishen Cheng, Avondale Estates, GA (US); Trevor Dimicco, Providence, RI (US); Audrey Earnshaw, Erie, CO (US); Juan C. Tapia, Larenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 17 days.

(21) Appl. No.: 17/556,907

(22) Filed: Dec. 20, 2021

(65) Prior Publication Data
US 2022/0192565 A1 Jun. 23, 2022

Related U.S. Application Data

(60) Provisional application No. 63/129,312, filed on Dec. 22, 2020.

(51) Int. Cl.
*E03D 11/02* (2006.01)
*A61B 5/20* (2006.01)
(Continued)

(52) U.S. Cl.
CPC ............ *A61B 5/208* (2013.01); *E03D 11/025* (2013.01); *E03D 13/005* (2013.01); *G01F 23/2962* (2013.01); *E03D 9/00* (2013.01)

(58) Field of Classification Search
CPC .. A47K 3/26; A61B 10/007; A61B 5/20–208; E03D 11/10; E03D 13/005; G01F 23/2962
See application file for complete search history.

(56) References Cited

U.S. PATENT DOCUMENTS

| | | | |
|---|---|---|---|
| 3,661,143 A | | 5/1972 | Henkin |
| 3,781,920 A | * | 1/1974 | Browne .................. E03D 11/10 4/441 |

(Continued)

FOREIGN PATENT DOCUMENTS

| | | |
|---|---|---|
| CA | 2882654 A1 | 10/2007 |
| CN | 2445749 Y | 9/2001 |

(Continued)

OTHER PUBLICATIONS

U.S. Appl. No. 15/748,107, filed Jan. 26, 2018 Notice of Allowance dated Dec. 12, 2022.

(Continued)

*Primary Examiner* — David P Angwin
*Assistant Examiner* — Nicholas A Ros
(74) *Attorney, Agent, or Firm* — Rutan & Tucker LLP (57) ABSTRACT

Disclosed herein is an automated urinary output measuring system. The automated urinary output measuring system includes an automated urinary output measuring device configured to be suspended from a rim of a sanitary hardware device and receive a volume of voided urine. The automated urinary output measuring device can include a receiving trough having an opening, a door configured to cover the opening in a fluid tight seal, the door coupled to the receiving trough by a hinge, and a lip extending from the receiving trough configured to detachably couple the automated urinary output measuring device to the sanitary hardware device. The system can further include an ultrasonic measuring system having a console coupled to one or more ultrasonic sensors, and a flushing mechanism coupled to the sanitary hardware device.

13 Claims, 7 Drawing Sheets

(51) Int. Cl.
 *E03D 13/00* (2006.01)
 *G01F 23/2962* (2022.01)
 *E03D 9/00* (2006.01)

(56) References Cited

U.S. PATENT DOCUMENTS

| | | | |
|---|---|---|---|
| 3,851,650 | A | 12/1974 | Darling |
| 3,919,455 | A | 11/1975 | Sigdell et al. |
| 4,276,889 | A | 7/1981 | Kuntz et al. |
| 4,286,590 | A | 9/1981 | Murase |
| 4,291,692 | A | 9/1981 | Bowman et al. |
| 4,296,749 | A | 10/1981 | Pontifex |
| 4,305,405 | A | 12/1981 | Meisch |
| 4,312,352 | A | 1/1982 | Meisch et al. |
| 4,343,316 | A | 8/1982 | Jespersen |
| 4,443,219 | A | 4/1984 | Meisch et al. |
| 4,448,207 | A * | 5/1984 | Parrish ............... G01F 23/2962 |
| | | | 600/584 |
| 4,509,366 | A | 4/1985 | Matsushita et al. |
| 4,532,936 | A | 8/1985 | LeVeen et al. |
| 4,658,834 | A | 4/1987 | Blankenship et al. |
| 4,723,950 | A | 2/1988 | Lee |
| 4,834,706 | A | 5/1989 | Beck et al. |
| 4,850,375 | A | 7/1989 | Rosenberg |
| 4,889,532 | A | 12/1989 | Metz et al. |
| 5,002,541 | A | 3/1991 | Conkling et al. |
| 5,409,014 | A | 4/1995 | Napoli et al. |
| 5,586,085 | A * | 12/1996 | Lichte ..................... G01F 25/20 |
| | | | 367/908 |
| 5,725,515 | A | 3/1998 | Propp |
| 5,733,319 | A | 3/1998 | Neilson et al. |
| 5,738,656 | A | 4/1998 | Wagner |
| 5,747,824 | A | 5/1998 | Jung et al. |
| 5,769,087 | A | 6/1998 | Westphal et al. |
| 5,807,278 | A | 9/1998 | McRae |
| 5,823,972 | A | 10/1998 | McRae |
| 5,891,051 | A | 4/1999 | Han et al. |
| 5,911,786 | A | 6/1999 | Nielsen et al. |
| 6,129,684 | A | 10/2000 | Sippel et al. |
| 6,132,407 | A | 10/2000 | Genese et al. |
| 6,250,152 | B1 | 6/2001 | Klein et al. |
| 6,256,532 | B1 | 7/2001 | Cha |
| 6,261,254 | B1 | 7/2001 | Baron et al. |
| 6,434,418 | B1 | 8/2002 | Neal et al. |
| 6,579,247 | B1 | 6/2003 | Abramovitch et al. |
| 6,592,612 | B1 | 7/2003 | Samson et al. |
| 6,709,420 | B1 | 3/2004 | Lincoln et al. |
| 6,716,200 | B2 | 4/2004 | Bracken et al. |
| 7,011,634 | B2 | 3/2006 | Paasch et al. |
| 7,161,484 | B2 | 1/2007 | Tsoukalis |
| 7,437,945 | B1 | 10/2008 | Feller |
| 7,442,754 | B2 | 10/2008 | Tepper et al. |
| 7,739,907 | B2 | 6/2010 | Boiarski |
| 7,871,385 | B2 | 1/2011 | Levinson |
| 7,931,630 | B2 | 4/2011 | Nishtala et al. |
| 7,976,533 | B2 | 7/2011 | Larsson |
| 7,998,126 | B1 | 8/2011 | Fernandez |
| 8,295,933 | B2 | 10/2012 | Gerber et al. |
| 8,328,733 | B2 | 12/2012 | Forte et al. |
| 8,328,734 | B2 | 12/2012 | Salvadori et al. |
| 8,337,476 | B2 | 12/2012 | Greenwald et al. |
| 8,374,688 | B2 | 2/2013 | Libbus et al. |
| 8,403,884 | B2 | 3/2013 | Nishtala |
| 8,471,231 | B2 | 6/2013 | Paz |
| 8,663,128 | B2 | 3/2014 | Paz et al. |
| 8,773,259 | B2 | 7/2014 | Judy et al. |
| 8,790,277 | B2 | 7/2014 | Elliott et al. |
| 8,790,320 | B2 | 7/2014 | Christensen |
| 8,790,577 | B2 | 7/2014 | Mizumoto et al. |
| 8,813,551 | B2 | 8/2014 | Boiarski |
| 8,827,924 | B2 | 9/2014 | Paz et al. |
| 8,832,558 | B2 | 9/2014 | Cardarelli et al. |
| 8,900,196 | B2 | 12/2014 | Andino |
| 9,045,887 | B2 * | 6/2015 | O'Malley ............... E03D 11/10 |
| 9,050,046 | B2 | 6/2015 | Elliott et al. |
| 9,074,920 | B2 | 7/2015 | Mendels et al. |
| 9,216,242 | B2 | 12/2015 | Nishtala et al. |
| 9,480,821 | B2 | 11/2016 | Ciccone et al. |
| 9,592,034 | B2 * | 3/2017 | Hall ...................... A61B 10/007 |
| 9,642,987 | B2 | 5/2017 | Bierman et al. |
| 9,731,097 | B2 | 8/2017 | Andino et al. |
| 9,895,095 | B2 | 2/2018 | Chen |
| 9,962,516 | B2 | 5/2018 | Lampotang et al. |
| 10,182,747 | B2 | 1/2019 | Charlez et al. |
| 10,245,008 | B2 | 4/2019 | Paige |
| 10,362,981 | B2 | 7/2019 | Paz et al. |
| 10,383,606 | B1 * | 8/2019 | McCord ................ G01N 33/493 |
| 10,448,875 | B2 | 10/2019 | Holt et al. |
| 11,703,365 | B2 | 7/2023 | Tourchak et al. |
| 2001/0056226 | A1 | 12/2001 | Zodnik et al. |
| 2002/0016719 | A1 | 2/2002 | Nemeth et al. |
| 2002/0161314 | A1 | 10/2002 | Sarajarvi |
| 2002/0193760 | A1 | 12/2002 | Thompson |
| 2003/0000303 | A1 | 1/2003 | Livingston et al. |
| 2003/0163183 | A1 | 8/2003 | Carson |
| 2003/0163287 | A1 | 8/2003 | Vock et al. |
| 2004/0267086 | A1 | 12/2004 | Anstadt et al. |
| 2005/0020958 | A1 | 1/2005 | Paolini et al. |
| 2005/0065583 | A1 | 3/2005 | Voorhees et al. |
| 2005/0172712 | A1 | 8/2005 | Nyce |
| 2005/0247121 | A1 | 11/2005 | Pelster |
| 2006/0100743 | A1 | 5/2006 | Townsend et al. |
| 2007/0010797 | A1 | 1/2007 | Nishtala et al. |
| 2007/0145137 | A1 | 6/2007 | Mrowiec |
| 2007/0252714 | A1 | 11/2007 | Rondoni et al. |
| 2008/0312556 | A1 * | 12/2008 | Dijkman ................ A61B 5/208 |
| | | | 600/584 |
| 2009/0056020 | A1 | 3/2009 | Caminade et al. |
| 2009/0099629 | A1 | 4/2009 | Carson et al. |
| 2009/0157430 | A1 | 6/2009 | Rule et al. |
| 2009/0287170 | A1 | 11/2009 | Otto |
| 2009/0315684 | A1 | 12/2009 | Sacco et al. |
| 2010/0094204 | A1 | 4/2010 | Nishtala |
| 2010/0130949 | A1 | 5/2010 | Garcia |
| 2010/0137743 | A1 | 6/2010 | Nishtala et al. |
| 2011/0113540 | A1 * | 5/2011 | Plate ........................ E03D 9/08 |
| | | | 4/300 |
| 2011/0120219 | A1 | 5/2011 | Barlesi et al. |
| 2011/0178425 | A1 | 7/2011 | Nishtala et al. |
| 2011/0238042 | A1 | 9/2011 | Davis et al. |
| 2011/0251572 | A1 | 10/2011 | Nishtala et al. |
| 2011/0263952 | A1 | 10/2011 | Bergman et al. |
| 2012/0029408 | A1 | 2/2012 | Beaudin |
| 2012/0059286 | A1 | 3/2012 | Hastings et al. |
| 2012/0078137 | A1 | 3/2012 | Mendels et al. |
| 2012/0078235 | A1 | 3/2012 | Martin et al. |
| 2012/0095304 | A1 | 4/2012 | Biondi |
| 2012/0109008 | A1 | 5/2012 | Charlez et al. |
| 2012/0123233 | A1 | 5/2012 | Cohen |
| 2012/0127103 | A1 | 5/2012 | Qualey et al. |
| 2012/0226196 | A1 | 9/2012 | DiMino et al. |
| 2012/0234434 | A1 | 9/2012 | Woodruff et al. |
| 2012/0302917 | A1 | 11/2012 | Fitzgerald et al. |
| 2012/0323502 | A1 | 12/2012 | Tanoura et al. |
| 2013/0066166 | A1 | 3/2013 | Burnett et al. |
| 2013/0109927 | A1 | 5/2013 | Menzel |
| 2013/0109928 | A1 | 5/2013 | Menzel |
| 2013/0131610 | A1 | 5/2013 | Dewaele et al. |
| 2013/0218106 | A1 | 8/2013 | Coston et al. |
| 2013/0245498 | A1 | 9/2013 | Delaney et al. |
| 2013/0267871 | A1 | 10/2013 | Delaney et al. |
| 2014/0039348 | A1 | 2/2014 | Bullington et al. |
| 2014/0155781 | A1 | 6/2014 | Bullington et al. |
| 2014/0155782 | A1 | 6/2014 | Bullington et al. |
| 2014/0159921 | A1 | 6/2014 | Qualey et al. |
| 2014/0207085 | A1 | 7/2014 | Brandt et al. |
| 2014/0243635 | A1 | 8/2014 | Arefieg |
| 2014/0335490 | A1 | 11/2014 | Baarman et al. |
| 2015/0343173 | A1 | 12/2015 | Tobescu et al. |
| 2015/0359522 | A1 | 12/2015 | Recht et al. |
| 2015/0362351 | A1 | 12/2015 | Joshi et al. |
| 2016/0051176 | A1 | 2/2016 | Ramos et al. |
| 2016/0183819 | A1 | 6/2016 | Burnett et al. |
| 2017/0100068 | A1 | 4/2017 | Kostov |

(56) References Cited

U.S. PATENT DOCUMENTS

| | | |
|---|---|---|
| 2017/0196478 A1 | 7/2017 | Hunter |
| 2017/0202698 A1 | 7/2017 | Zani et al. |
| 2017/0249445 A1 | 8/2017 | Devries et al. |
| 2017/0290540 A1 | 10/2017 | Franco |
| 2017/0291012 A1 | 10/2017 | Iglesias |
| 2017/0307423 A1 | 10/2017 | Pahwa et al. |
| 2018/0015251 A1 | 1/2018 | Lampotang et al. |
| 2018/0280236 A1 | 10/2018 | Ludin et al. |
| 2018/0344234 A1 | 12/2018 | McKinney et al. |
| 2019/0046102 A1 | 2/2019 | Kushnir et al. |
| 2019/0069830 A1 | 3/2019 | Holt et al. |
| 2019/0126006 A1 | 5/2019 | Rehm et al. |
| 2019/0201596 A1 | 7/2019 | Luxon et al. |
| 2019/0223844 A1* | 7/2019 | Aboagye ............. A61B 10/007 |
| 2019/0247236 A1 | 8/2019 | Sides et al. |
| 2019/0321588 A1 | 10/2019 | Burnett et al. |
| 2019/0328945 A1 | 10/2019 | Analytis et al. |
| 2019/0358387 A1 | 11/2019 | Elbadry et al. |
| 2019/0365308 A1 | 12/2019 | Laing et al. |
| 2019/0381223 A1 | 12/2019 | Culbert et al. |
| 2020/0022637 A1 | 1/2020 | Kurzrock et al. |
| 2020/0085378 A1 | 3/2020 | Burnett et al. |
| 2020/0268303 A1* | 8/2020 | Oliva ..................... A61B 5/202 |
| 2020/0289749 A1 | 9/2020 | Odashima et al. |
| 2021/0077007 A1 | 3/2021 | Jouret et al. |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2022/0192564 A1 | 6/2022 | Kriscovich et al. |
| 2022/0192566 A1 | 6/2022 | Cheng et al. |
| 2022/0193375 A1 | 6/2022 | Rehm et al. |
| 2022/0296140 A1 | 9/2022 | Nguyen et al. |
| 2022/0386917 A1 | 12/2022 | Mann et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |

FOREIGN PATENT DOCUMENTS

| | | | |
|---|---|---|---|
| CN | 200951235 Y | 9/2007 | |
| CN | 201492414 U | 6/2010 | |
| CN | 102647939 A | 8/2012 | |
| CN | 109498013 A | 3/2019 | |
| CN | 110859636 A | 3/2020 | |
| CN | 112426156 A | 3/2021 | |
| EP | 0342028 A2 | 11/1989 | |
| ES | 2760470 * | 5/2020 | ............. A61B 5/208 |
| GB | 2576743 A | 3/2020 | |
| JP | S49-75171 A | 7/1974 | |
| JP | S54-147066 A | 11/1979 | |
| JP | S58-190719 A | 11/1983 | |
| JP | S60-219517 A | 11/1985 | |
| JP | H02-057240 B2 | 12/1990 | |
| JP | H08-271301 A | 10/1996 | |
| JP | H10-104041 A | 4/1998 | |
| JP | 2007-303982 A | 11/2007 | |
| JP | 2008-524618 A | 7/2008 | |
| JP | 2009-068959 A | 4/2009 | |
| JP | 2010-121950 A | 6/2010 | |
| JP | 2010-530978 A | 9/2010 | |
| JP | 2012-105947 A | 6/2012 | |
| JP | 2012-225790 A | 11/2012 | |
| WO | 1981003427 A1 | 12/1981 | |
| WO | 2004045410 A1 | 6/2004 | |
| WO | 2013013782 A2 | 1/2013 | |
| WO | 20130178742 A1 | 12/2013 | |
| WO | 2014/043650 A2 | 3/2014 | |
| WO | 2014108690 A1 | 7/2014 | |
| WO | 2014/135856 A1 | 9/2014 | |
| WO | 2014/151068 A2 | 9/2014 | |
| WO | 2014145971 A2 | 9/2014 | |
| WO | 201511402 A1 | 1/2015 | |
| WO | 2015/105916 A1 | 7/2015 | |
| WO | 2015/127390 A1 | 8/2015 | |
| WO | 2016177901 A1 | 11/2016 | |
| WO | 2017/023794 A1 | 2/2017 | |
| WO | 2018156624 A1 | 8/2018 | |
| WO | 2019066357 A1 | 4/2019 | |
| WO | 2019/226697 A1 | 11/2019 | |
| WO | 2020154370 A1 | 7/2020 | |
| WO | 2022108589 A1 | 5/2022 | |
| WO | 2022182794 A1 | 9/2022 | |

OTHER PUBLICATIONS

U.S. Appl. No. 17/054,493, filed Nov. 10, 2020 Non-Final Office Action dated Jan. 27, 2023.
U.S. Appl. No. 17/3026,821, filed May 3, 2021 Non-Final Office Action dated Jan. 10, 2023.
U.S. Appl. No. 17/373,535, filed Jul. 12, 2021 Non-Final Office Action dated Nov. 9, 2022.
Bard Medical, Criticore Disposables—Non I.C., 3 pages, www.bardmedical.com/products/patienl-moniloring-,ystems/criticore@-system/criticore@ disposables-non-ic/ Jan. 30, 2015.
Bard Medical, Criticore Infection Control Disposables, 3 pages, www.bardmedical.com/patienl-monitoring-,ystems/criticore@-system/criticore®-infection-control-disposables/ Jan. 30, 2015.
Bard Medical, Criticore Monitor, 11 pages, www.bardmedical.com/products/patient-monitoring-systems/criticore®-monitor/ Jan. 30, 2015.
Bard Medical, Urine Meiers, 3 pages, www.bardmedical.com/products/urological-drainage/urine-collection/urinemeters/Jan. 30, 2015.
Biometrix, Urimetrix, 4 pages, www.biometrixmedical.com/Products/56/Urimetrix%E2%84%A2 Oct. 29, 2014.
Observe Medical, sippi, 3 pages, www.observemedical.com/products.html Oct. 29, 2014.
PCT/US19/33389 filed May 21, 2019 International Search Report and Written Opinion dated Aug. 2, 2019.
PCT/US2016/044835 filed Jul. 20, 2016 International Search Report and Written Opinion dated Dec. 16, 2016.
U.S. Appl. No. 17/054,493, filed Nov. 10, 2020 Final Office Action dated May 31, 2022.
U.S. Appl. No. 15/748,107, filed Jan. 26, 2018 Final Office Action dated Dec. 23, 2020.
U.S. Appl. No. 15/748, 107, filed Jan. 26, 2018 Final Office Action dated Feb. 7, 2022.
U.S. Appl. No. 15/748, 107, filed Jan. 26, 2018 Non-Final Office Action dated Sep. 3, 2021.
U.S. Appl. No. 15/748,107, filed Jan. 26, 2018 Non-Final Office Action dated Sep. 4, 2020.
U.S. Appl. No. 17/054,493, filed Nov. 10, 2020 Non-Final Office Action dated Nov. 24, 2021.
PCT/US2019/045787 filed Aug. 8, 2019 International Preliminary Report on Patentability dated Feb. 16, 2021.
PCT/US2019/045787 filed Aug. 8, 2019 International Search Report and Written Opinion dated Oct. 2, 2019.
PCT/US20/61367 filed Nov. 19, 2020 International Search Report and Written Opinion dated Feb. 22, 2021.
U.S. Appl. No. 17/262,080, filed Jan. 21, 2021 Non-Final Office Action dated Apr. 6, 2023.
U.S. Appl. No. 17/373,535, filed Jul. 12, 2021 Notice of Allowance dated Feb. 23. 2023.
DFree Personal—Consumer Product Brochure, 2019.
DFree Pro Brochure 2019.
Leonhäuser, D et al., "Evaluation of electrical impedance tomography for determination of urinary bladder vol. comparison with standard ultrasound methods in healthy volunteers."—BioMed Engr On-line; 17:95; 2018.
Li, R., et al., "Design of a Noninvasive Bladder Urinary vol. Monitoring System Based on Bio-Impedance."—Engineering; vol. 5; pp. 321-325; 2013.
PCT/US2022/017574 filed Feb. 23, 2022 Internation Search Report and Written Opinion dated Jun. 8, 2022.

(56) References Cited

OTHER PUBLICATIONS

Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.
Schlebusch, T. et al., "Bladder vol. estimation from electrical impedance tomography" Physiological Measurement, Institute of Physics, Bristol, GB. vol. 35 No. 9 Aug. 20, 2014. (Aug. 20, 2014).
SECA product catalog, https://us.secashop.com/products/seca-mbca/seca-mbca-514/5141321139, last accessed Sep. 11, 2020.
U.S. Appl. No. 17/054,493, filed Nov. 10, 2020 Final Office Action dated Oct. 4, 2023.
U.S. Appl. No. 17/262,080, filed Jan. 21, 2021 Final Office Action dated Sep. 11, 2023.
U.S. Appl. No. 17/262,080, filed Jan. 21, 2021 Notice of Allowance dated Oct. 13, 2023.
U.S. Appl. No. 17/306,821, filed May 3, 2021 Advisory Action dated Oct. 3, 2023.
U.S. Appl. No. 17/306,821, filed May 3, 2021 Final Office Action dated Jul. 19, 2023.
U.S. Appl. No. 17/373,546, filed Jul. 12, 2021 Non-Final Office Action dated Nov. 1, 2023.

\* cited by examiner

AUTOMATED URINARY OUTPUT MEASURING SYSTEM

PRIORITY

This application claims the benefit of priority to U.S. Provisional Application No. 63/129,312, filed Dec. 22, 2020, which is incorporated by reference in its entirety into this application.

BACKGROUND

Low urinary output in congestive heart failure ("CHF") patients can be a symptom of low cardiac output. It can be difficult to non-invasively measure urinary output in CHF patients, as some CHF patients can be ambulatory and most automated urinary output measuring devices are invasive and engineered for non-ambulatory patients in the intensive care unit. It would be beneficial to the CHF patient and their clinician to be able to accurately measure and track urinary output in ambulatory patients. Disclosed herein are a system and method of use that address the foregoing.

SUMMARY

Disclosed herein is an automated urinary output measuring system. The automated urinary output measuring system includes an automated urinary output measuring device configured to be suspended from a rim of a sanitary hardware device and receive a volume of voided urine. The automated urinary output measuring device includes a receiving trough having an opening, a door configured to cover the opening in a fluid tight seal, the door coupled to the receiving trough by a hinge, and a lip extending from the receiving trough configured to detachably couple the automated urinary output measuring device to the sanitary hardware device. The system further includes an ultrasonic measuring system having a console coupled to one or more ultrasonic sensors, and a flushing mechanism coupled to the sanitary hardware device, having a button configured to activate flushing of the sanitary hardware device.

In some embodiments, the sanitary hardware device includes a toilet.

In some embodiments, the receiving trough includes a front wall and a back wall, with the opening located at a bottom of the back wall and the lip extending from the front wall.

In some embodiments, the door may be configured to transition between an opened configuration and a closed configuration.

In some embodiments, the door is biased toward the closed configuration.

In some embodiments, in the closed configuration, the door creates the fluid tight seal over the opening.

In some embodiments, the door extends past the opening to contact a surface of the sanitary hardware device.

In some embodiments, the flushing mechanism is in communication with the console.

In some embodiments, the console includes one or more processors, non-transitory computer readable medium, an energy source and a plurality of logic modules.

In some embodiments, the plurality of logic modules when executed by the processor, are configured to perform operations including one or more of the following: activating the one or more ultrasonic sensors, receiving the measured time of reflection values from the one or more ultrasonic sensors, determining the volume of urine within the receiving trough, correlating the measured time of reflection value with a volume value and a time of day value, configuring the door between the opened configuration and the closed configuration, and transmitting the volume value and the time of day value to a computing device.

In some embodiments, a volume of flushing water from the sanitary hardware device is configured to transition the door from the closed configuration to the opened configuration.

In some embodiments, the user is configured to transition the door from the closed configuration to the opened configuration.

In some embodiments, the console is configured to transition the door from the closed configuration to the opened configuration.

In some embodiments, the console is coupled to the receiving trough.

In some embodiments, the console is located within the flushing mechanism.

Also disclosed herein is a method of measuring urinary output, comprising acquiring a volume of voided urine in a receiving trough of an automated urinary output measuring device, the receiving trough having a lip, an opening, a door coupled to the trough by a hinge and configured to cover the opening in a fluid tight seal; the receiving trough suspended from a rim of a sanitary hardware device, measuring the whole volume of voided urine using an ultrasonic measuring system including one or more ultrasonic sensors coupled to a console, transmitting a volume value and time of day value to a computing device, and disposing of the whole volume of voided urine through the opening into the sanitary hardware device.

In some embodiments, measuring the volume of voided urine includes using the one or more ultrasonic sensors to generate one or more ultrasonic waves towards an air/urine interface and measuring the time of reflection of the one or more ultrasonic waves from the air/urine interface to the one or more ultrasonic sensors.

In some embodiments, the receiving trough includes a back wall and the opening is located at the bottom of the back wall.

In some embodiments, the door extends past the opening to contact a portion of the sanitary hardware device.

In some embodiments, disposing of the volume of voided urine includes transitioning the door from a closed configuration to an opened configuration.

In some embodiments, transitioning the door from the closed configuration to the opened configuration breaks the fluid tight seal.

In some embodiments, transitioning the door from the closed configuration to the opened configuration includes allowing a volume of flushing water from the sanitary hardware device to transition the door from the closed configuration to the opened configuration.

In some embodiments, transitioning the door from the closed configuration to the opened configuration includes the user transitioning the door from the closed configuration to the opened configuration.

In some embodiments, transitioning the door from the closed configuration to an opened configuration includes the console transitioning the door from the closed configuration to the opened configuration.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

Unless defined otherwise, all technical and scientific terms used herein have the same meaning as commonly understood by those of ordinary skill in the art.

Figure 1A:
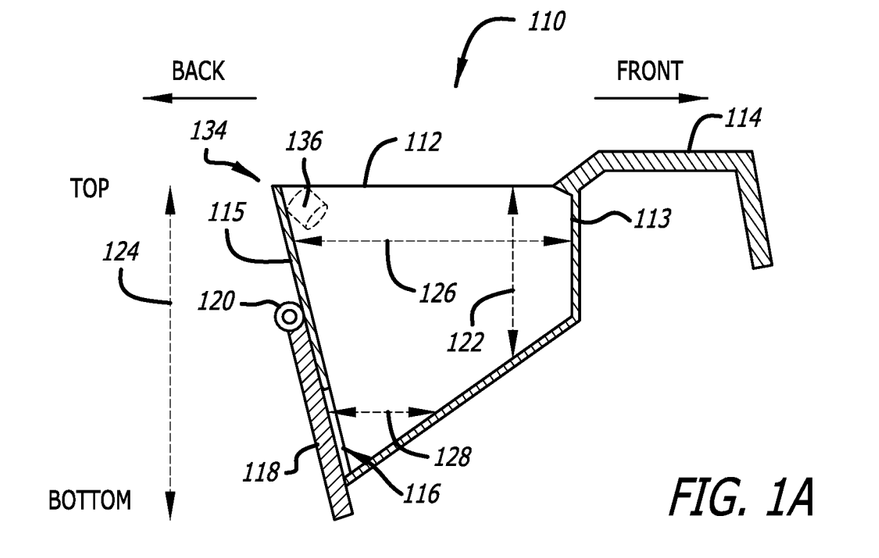
FIG. 1A illustrates a cross sectional side view of an automated urinary output measuring device, in accordance with some embodiments.

FIG. 1A illustrates a cross sectional side view of an automated urinary output measuring device 110 of an automated urinary output measuring system 100 (Refer to FIG. 5A-5B), in accordance with some embodiments. In some embodiments, the automated urinary output measuring device ("device") 110 includes a receiving trough 112 configured to receive and contain a volume of voided urine. In some embodiments, the automated urinary output measuring system 100 may be configured to detect and measure the volume of voided urine captured within the receiving trough 112. In some embodiments, the receiving trough 112 may be configured to be suspended from a rim of a sanitary hardware device that will be described in more detail herein. The receiving trough 112 includes a front, a back, a top and a bottom, as orientated from a user standing in front of the receiving trough 112. It can be appreciated that a user may also contribute a volume of voided urine to the receiving trough 112 from above the receiving trough 112 as opposed to in front of the receiving trough 112, which is also contemplated. The receiving trough 112 includes a front wall 113 and a back wall 115. In some embodiments, a lip 114 extends from the receiving trough 112. In some embodiments, the lip 114 may extend from the front wall 113 and may be configured to allow the device 110 to be suspended from a rim of a sanitary hardware device 140 (Refer to FIG. 2B.) and be stabilized within the sanitary hardware device 140 that will be described in more detail herein.

In some embodiments, the receiving trough 112 includes an opening 116 and a door 118. The door 118 may be coupled to the receiving trough 112 by a hinge 120. In some embodiments, the opening 116 is located at the bottom of the back wall 115 and may be configured to allow passage of fluids therethrough. The door 118 may be coupled to back wall 115 of the receiving trough 112 and be configured to cover the opening 116 in a fluid tight seal and prevent fluid passage therethrough. In some embodiments, the hinge 120 may be configured to allow the door 118 to move between a closed configuration, wherein the door 118 seals the opening 116 to prevent any portion of any fluid to pass therethrough and an opened configuration, wherein the door 118 is released from the opening 116 to release a volume of fluid within the receiving trough 112 into the sanitary hardware device 140 that will be described in more detail herein. In some embodiments, the door 118 may be transitioned from the closed configuration to the opened configuration by the user. In some embodiments, the door 118 may be biased towards the closed configuration by a spring, a magnet, or the like. In an embodiment, the opening 116 may include one or more magnets and the door 118 may include ferrous elements to generate the fluid tight seal. The fluid tight seal may be configured to be broken by a pushing force configured to transition the door 118 from the closed configuration to the opened configuration.

In some embodiments, the door 118 may extend past the opening 116 or overhang the receiving trough 112 to contact a portion of the sanitary hardware device 140, that will be described in more detail herein. In some embodiments, the back wall 115 of the device 110 may be angled from top to bottom towards the front wall 113 of the device 110.

In some embodiments, the receiving trough 112 includes an ultrasonic measuring system 134 having one or more ultrasonic sensors 136 configured to generate and detect ultrasonic waves and a console. In some embodiments, the ultrasonic measuring system 134 may be configured to measure a volume of voided urine within the receiving trough 112. In some embodiments, the one or more ultrasonic sensors 136 may be located towards the top of the receiving trough 112. In an embodiment, the ultrasonic measuring system 134 may be configured to be removable from the receiving trough 112. In some embodiments, the device 110 or the receiving trough 112 may be disposable or reusable. In some embodiments, the device 110 may be configured to be sterilized between uses. In some embodiments, portions of the device 110 including the receiving trough 112 may be constructed of plastic polymers such as polyethylene, polypropylene, polystyrene or the like. In some embodiments, the device 110 including portions of the receiving trough 112 may be constructed of plastic or metal such aluminum, stainless steel, or the like.

In some embodiments, the receiving trough 112 includes a first depth 122 located at the front of the receiving trough 112 and second depth 124 located at the back of the receiving trough 112. The second depth 124 is greater than the first depth 122. The receiving trough 112 may be configured to slope from the first depth 122 to the second depth 124. In some embodiments, the receiving trough 112 may be configured to slope from the first depth 122 to the second depth 124 at the bottom of the receiving trough 112. In some embodiments, the receiving trough 112 may be configured to gradually slope from the first depth 122 to the second depth 124. In some embodiments, the receiving trough 112 may be configured into a shape that is configured to funnel all the liquid to the bottom of the trough 112. In some embodiments, the receiving trough 112 includes a first length 126 located at the top of the receiving trough 112 and a second length 128 located at the bottom of the receiving trough 112. In some embodiments, the first length 126 is larger than the second length 128. In some embodiments, the receiving trough 112 may be configured to slope from the first length 126 to the second length 128.

Figure 1B:
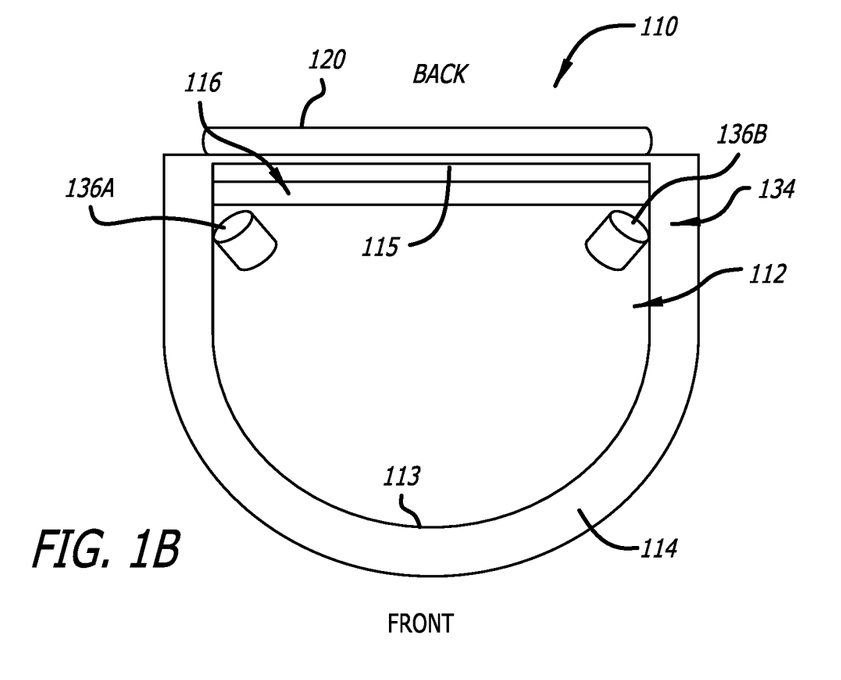
FIG. 1B illustrates a plan view of the automated urinary output measuring device, in accordance with some embodiments.

FIG. 1B illustrates a plan view of the automated urinary output measuring device 110, in accordance with some embodiments. In some embodiments, the receiving trough 112 may be in the shape of a quarter cylinder, a half spheroid, a half sphere, an irregular polygon or the like. In some embodiments, the lip 114 extends from the front wall 113. In an embodiment, as illustrated in FIG. 1B, the lip 114 may be configured to extend from the receiving trough 112 to contact the sanitary hardware device 140. In some embodiments, the lip 114 may extend from a portion of the front wall 113. In some embodiments, the lip 114 may extend from the entire front of the receiving trough 112. In some embodiments, as illustrated in FIG. 1B, the opening 116, the door 118 and the hinge 120 may be configured to extend across the entire back wall 115. In some embodiments, the opening 116, the door 118 or the hinge 120 may be configured to extend along a portion of the back wall 115.

The ultrasonic measuring system 134 includes the one or more ultrasonic sensors 136 configured to generate and detect an ultrasonic wave, the one or more ultrasonic sensors being coupled to a console 160 that will be described in more detail herein (Refer to FIG. 3A). In some embodiments, the ultrasonic measuring system 134 may be configured to measure urinary output. In some embodiments, the ultrasonic measuring system 134 may be configured so that a first ultrasonic sensor 136A may be laterally aligned with a second ultrasonic sensor 136B along the back wall 115. In some embodiments, the first ultrasonic sensor 136A may be laterally offset with the second ultrasonic sensor 136B along the back wall 115. In an embodiment, the first ultrasonic sensor 136A may be coupled to the front wall 113 and the second ultrasonic sensor 136B may be coupled to the back wall 115. It can be appreciated that the first ultrasonic sensor 136A and the second ultrasonic sensor 136B may be arranged in any number of configurations in the receiving trough 112, all of which are considered.

Figure 2A:
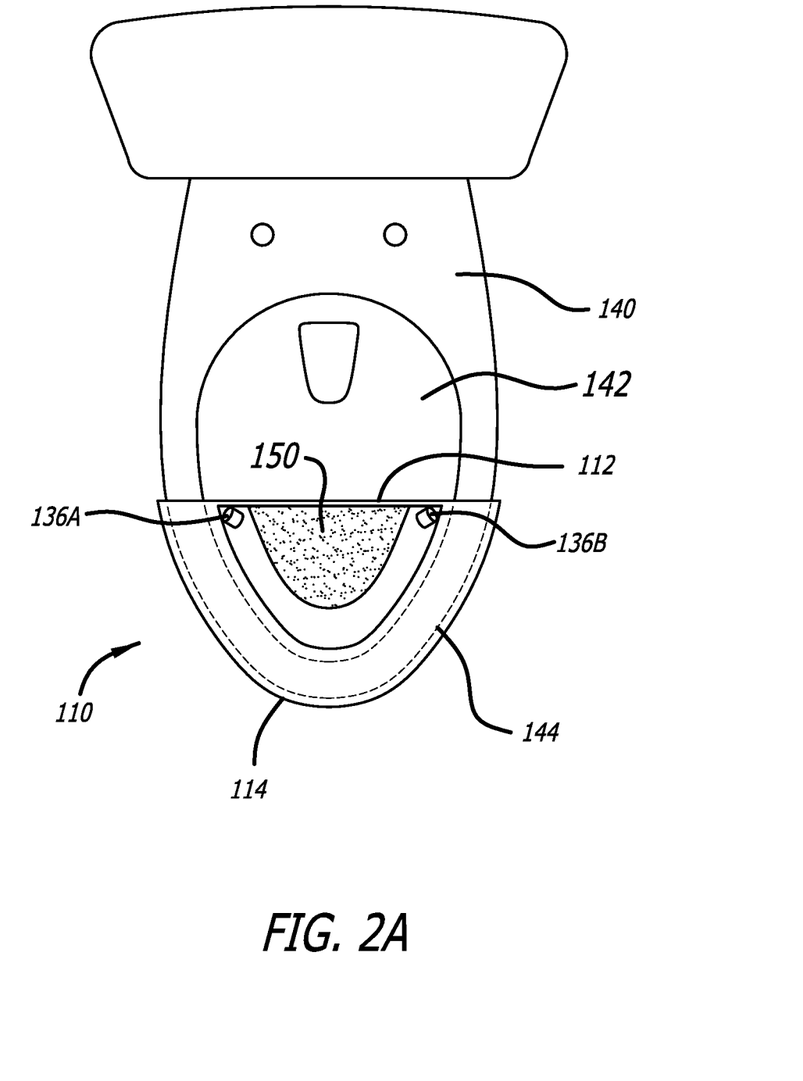
FIG. 2A illustrates a plan view of an automated urinary output measuring system within a sanitary hardware device, in accordance with some embodiments.

FIG. 2A illustrates a plan view of the automated urinary output measuring device 110 within the sanitary hardware device 140, in accordance with some embodiments. In some embodiments, the device 110 may be configured to be secured to the sanitary hardware device 140. As used herein, the sanitary hardware device 140 means a toilet including a flushing component although other sanitary hardware devices with or without a flushing component are considered including a urinal, a portable toilet, a latrine or the like. The toilet 140 includes a bowl 142 having a rim 144 surrounding the bowl 142. The lip 114 of the device 110 may be configured to be secured to a portion of the rim 144 of the toilet 140. In some embodiments, the lip 114 may be configured to orient the device 110 within the bowl 142. In some embodiments, the device 110 may be secured to a portion of the rim 144 through a press fit, a snap fit, a clamp mechanism, an interference fit or the like. In some embodiments, the device 110 may be detachably secured to the rim 144 and removed after the volume of voided urine has been disposed of. In some embodiments, the device 110 may occupy a portion of the bowl 142 or the entire bowl 142.

Figure 2B:
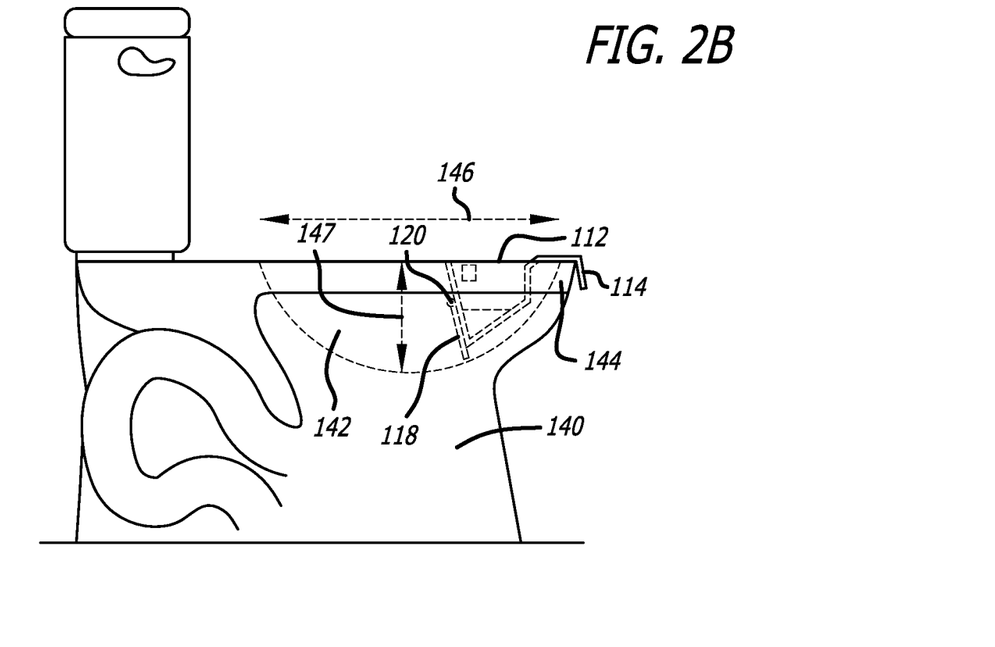
FIG. 2B illustrates a cross sectional side view of the automated urinary output measuring system within a toilet, in accordance with some embodiments.

FIG. 2B illustrates a cross sectional side view of the automated urinary output measuring device 110 in the toilet 140, in accordance with some embodiments. In some embodiments, the bowl 142 has a bowl length 146 and a bowl depth 147. In some embodiments, with the lip 114 being secured to the rim 144, the receiving trough 112 may be suspended within the bowl 142. In some embodiments, the door 118 may hang from the device 110 and just touch a portion of the bowl 142. In some embodiments, the door 118 may be configured to contact a portion of the bowl 142 and stabilize the device 110 therein. In some embodiments, as illustrated in FIG. 2B, the receiving trough 112 may be configured to cover at least a portion of the bowl length 146 and a least a portion of the bowl depth 147. In some embodiments, the receiving trough 112 may be configured to cover the entire bowl 142.

Figure 2C:
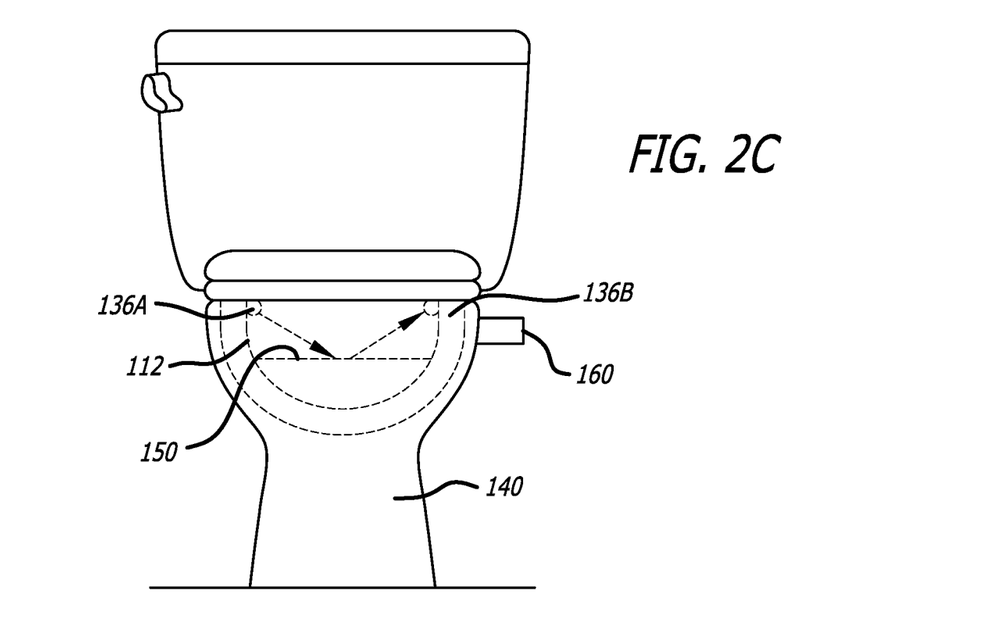
FIG. 2C illustrates a cross sectional front view of the automated urinary output measuring system within the toilet, in accordance with some embodiments.

FIG. 2C illustrates a cross sectional front view of an exemplary method of measuring urine output using the automated urinary output measuring device 110, in accordance with some embodiments. A user may void a volume of urine into the receiving trough 112. When the volume of voided urine is collected into the trough 112, the ultrasonic measuring system 134 may be configured to detect the volume of voided urine. In some embodiments, the whole volume of voided urine collected into the trough 112 may be measured with prescribed periodicity by a clinician. In some embodiments, the first ultrasonic sensor 136A may generate an ultrasound wave that travels through the air towards the volume of voided urine contained within the trough 112. Once the ultrasound wave contacts the air/urine interface 150 in the receiving trough 112, the ultrasound wave is reflected towards the second ultrasonic sensor 136B. The second ultrasonic sensor 136B may be configured to detect the reflected ultrasound wave at some time after the ultrasound wave was generated by the first ultrasonic sensor 136A. Each of the first ultrasonic sensor 136A and the second ultrasonic sensor 136B may be in communication with a console 160. In some embodiments, the console 160 may be configured to correlate the time from the generated wave to the detected wave with a volume of voided urine within the receiving trough 112 that will be described in more detail herein. In some embodiments, the console 160 may be detachably coupled to the toilet 140.

Figure 3A:
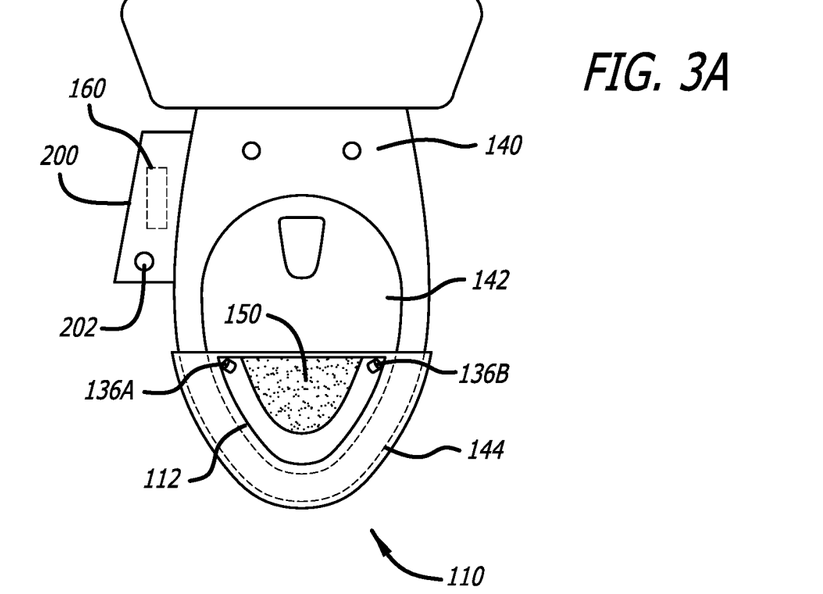
FIG. 3A illustrates a plan view of the automated urinary output measuring system within the toilet including a flushing mechanism, in accordance with some embodiments.
Figure 3B:
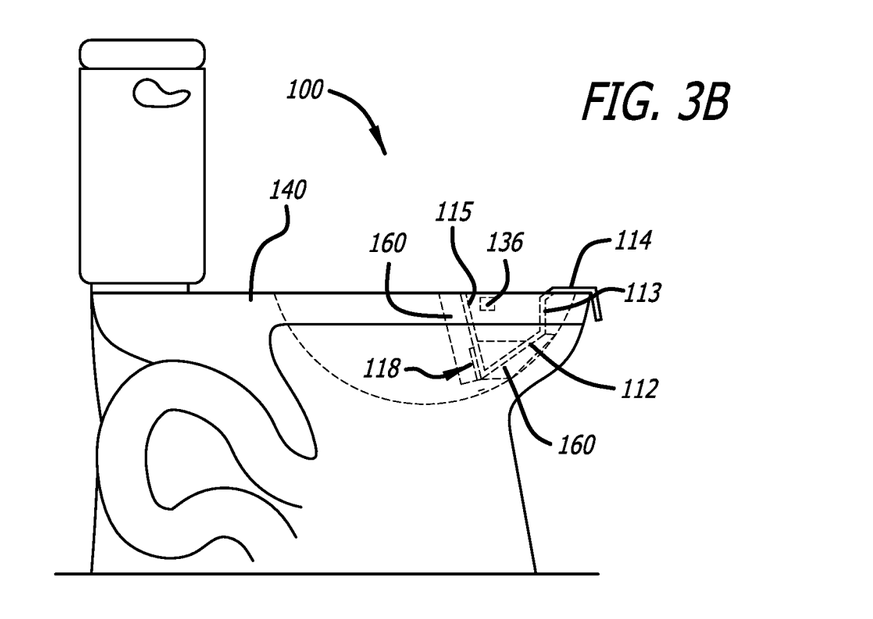
FIG. 3B illustrates a cross sectional side view of the automated urinary output measuring system within the toilet including a console, in accordance with some embodiments.

FIG. 3A illustrates a plan view of the automated urinary output measuring system 100 in the toilet 140 including a flushing mechanism 200, in accordance with some embodiments. The device 110 engages with the rim 144, so that the receiving trough 112 is suspended within the toilet bowl 142. In some embodiments, the system 100 includes a flushing mechanism 200 coupled to the toilet 140, which may be configured for flushing the toilet 140 with a volume of flushing water. In some embodiments, the flushing mechanism 200 may be coupled to the side or the back of the toilet 140. In some embodiments, the flushing mechanism 200 may include a button 202 that activates the flushing process. In some embodiments, the console 160 may be located within the flushing mechanism 200. In some embodiments, the console 160 may be configured to be in communication with or coupled to the button 202, in that when the button 202 is depressed to activate the flushing process, the console 160 may be configured to activate the first ultrasonic sensor 136A and the second ultrasonic sensor 136B to measure the volume of voided urine within the receiving trough 112. FIG. 3B illustrates a cross sectional side view of the automated urinary output measuring system 100, in accordance with some embodiments. In some embodiments, the console 160 may be coupled to the bottom of the receiving trough 112, the back wall 115 of the receiving trough 112, the front wall 113 of the receiving trough, the door 118 of the receiving trough 112 or the like.

Figure 4:
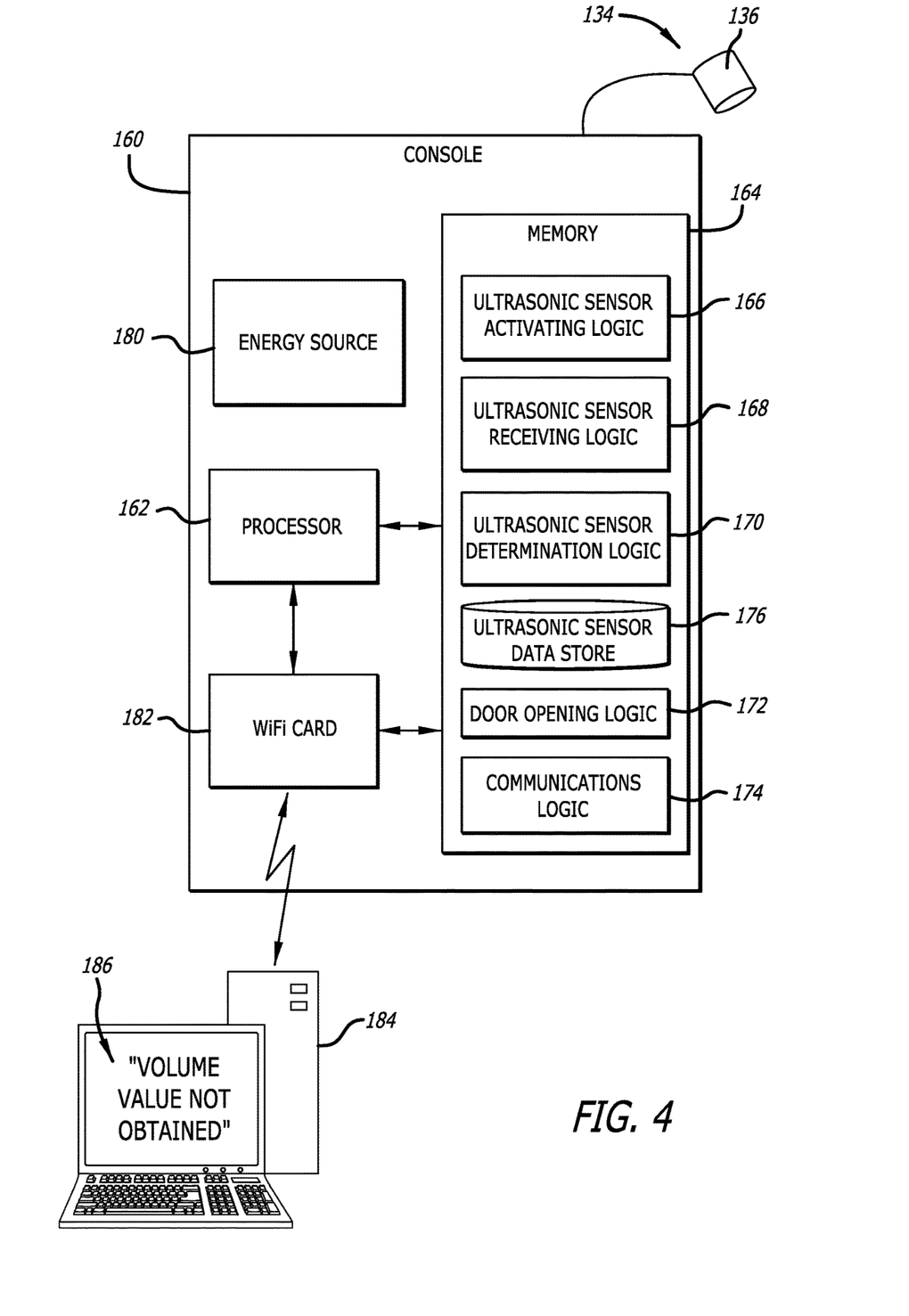
FIG. 4 illustrates a block diagram of various components of the ultrasonic measuring system including the console, in accordance with some embodiments.

FIG. 4 illustrates a block diagram of some components of the ultrasonic measuring system 134 including the console 160, in accordance with some embodiments. In some embodiments, the ultrasonic measuring system 134 includes the one or more ultrasonic sensors 136 and the console 160. In some embodiments, the console 160 includes one or more processors 162, non-transitory computer readable medium ("memory") 164, an energy source 180 and a plurality of logic modules. In some embodiments, the one or more processors 162 may be low consumption/energy efficient. In some embodiments, the inclusion of one or more processors that are low consumption/energy efficient may be configured to allow the entire console 160 to be energy efficient. In some embodiments, the energy source 180 may be configured to power the console 160. In some embodiments, the plurality of logic modules include one or more of: an ultrasonic sensor activating logic 166, an ultrasonic sensor receiving logic 168, an ultrasonic sensor determination logic 170, a door opening logic 172 and a communications logic 174. In some embodiments, the memory 164 includes one or more data stores including an ultrasonic sensor data store 176. In some embodiments, the ultrasonic sensor activating logic 166 may be configured to activate the one or more ultrasonic sensors 136. In some embodiments, the ultrasonic sensor activating logic 166 may be activated by the flushing mechanism 200 or the button 202.

In some embodiments, the ultrasonic sensor activating logic 166 may be activated by the user directly. In some embodiments, the ultrasonic sensor receiving logic 168 may be configured to receiving the measured time of reflection value from the one or more sensors 136. In some embodiments, the ultrasonic sensor determination logic 170 may be configured to determine the volume of voided urine within the receiving trough 112. In some embodiments, the ultrasonic sensor determination logic 170 may be configured to determine the volume of voided urine within the trough 112 by correlating the measured time of reflection value with a volume value corresponding to the volume of voided urine in the trough 112. In some embodiments, the ultrasonic sensor determination logic 170 may be further configured to associate a time of day value with the volume value at the time of day the volume value was determine. In some embodiments, the ultrasonic sensor determination logic 170 may be configured to generate an associated pairing of the {time of day value, volume value}. In some embodiments, wherein there are two of more ultrasonic sensors 136 in the ultrasonic measuring system 134, the ultrasonic sensor determination logic 170 may use the two or more ultrasonic sensors 136 to check the accuracy of the volume of fluid within the trough 112.

In some embodiments, where there are two or more ultrasonic sensors 136, the ultrasonic sensor determination logic 170 may be configured to report an error if one or more of the measured time of reflections values are above or below a threshold. In some embodiments, the threshold may be user-defined or automatically generated by the console 160. In some embodiments, the user defined threshold may be 1-5% of the measured time of reflection values, however it will be appreciated that greater or lesser increments are also contemplated. When the one or more measured time of reflection values are above or below the user defined threshold, it may signal the one or more ultrasonic sensors 136 may need maintenance, cleaning or replacement. In some embodiments, wherein there are two or more ultrasonic sensors 136, the ultrasonic sensor determination logic 170 may average the two or more measured time of reflection values and correlate the averaged two or more measured time of reflection values to one volume value in one {time of day value, volume value} or may correlate the measured time of reflection value from each ultrasonic sensor to a volume value in a {time of day value, volume value from first ultrasonic sensor 136A} pairing, and a {time of day value, volume value from second ultrasonic sensor 136B} pairing. In an embodiment, the ultrasonic determination logic 170 may be configured to generate an associated trio of the {time of day value, voiding number in a specific time period value, volume value}. For example, for a second voiding of the day wherein the measurement in the trough 112 is taken at 8:00 AM, the trio may read {8:00, 2, 75 mL}. In some embodiments, the ultrasonic determination logic 170 may be configured to correlate or associate additional parameters to the pairing of {time of day value, volume value} or the trio of {time of day value, voiding number in a specific day value, volume value} to create a quartet, quintet, sextet or the like. For example, the ultrasonic determination logic 170 may detect the status of the device 110 and may include the status of the device 110 in the trio as a quartet of {status of the device value, time of day value, voiding number value, volume value}. Although four values are demonstrated, greater or lesser number of values are also considered.

In some embodiments, the ultrasonic sensor data store 176 may be configured to store the associated pairings of the {time of day value, volume value}. In some embodiments, the ultrasonic sensor data store 176 may be configured to store the associated trio of the {time of day value, voiding number in the specific time period value, volume value} or the associated quartet of {status of device value, time of day value, voiding number in the specific time period value, volume value}. In an embodiment, the door 118 may be controlled by the console 160. In this embodiment, the door opening logic 172 may be configured to transition the door 118 between the opened configuration and the closed configuration. In this embodiment, the door opening logic 172 may be activated by the user. In this embodiment, the door opening logic 172 may be configured to transition the door 118 only when a complete and accurate determination of the volume of voided urine is obtained. For example, if the ultrasonic measuring system 134 is inactivated or blocked, the volume of voided urine may be kept in the receiving trough 112, until an accurate measurement is obtained.

In some embodiments, the communications logic 172 may be configured to transmit the associated pairing of {time of day value, volume value}, the associated trio of {time of day value, voiding number in the specific time period value, volume value} or the associated quartet of {status of the device, time of day value, voiding number in the specific time period value, volume value} to a computing device 184, an electronic medical record ("EMR") system or the like. In some embodiments, the communications logic 172 may transmit the associated pairing of {time of day value, volume value}, the associated trio of {time of day value, voiding number in the specific time period value, volume value} or the associated quartet of {status of the device, time of day value, voiding number in the specific time period value, volume value} at regular frequencies, regular time intervals or when a volume of fluid is detected within the trough 112. The communications logic 172 may be configured to wirelessly transmit the associated pairings of {time of day value, volume value} to the computing device 184. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like. In some embodiments, if a volume value is not obtained, the communications logic 172 may be configured to transmit a message 186 to the computing device 184, indicating a volume value was not obtained. In some embodiments, the console 160 may include a WiFi antenna 182 or WiFi card that may be configured to transmit data or the message 186 to a computing device 184 over a wireless network. In some embodiments, the message 186 may include text, a graphic or a combination thereof.

Figure 5A:
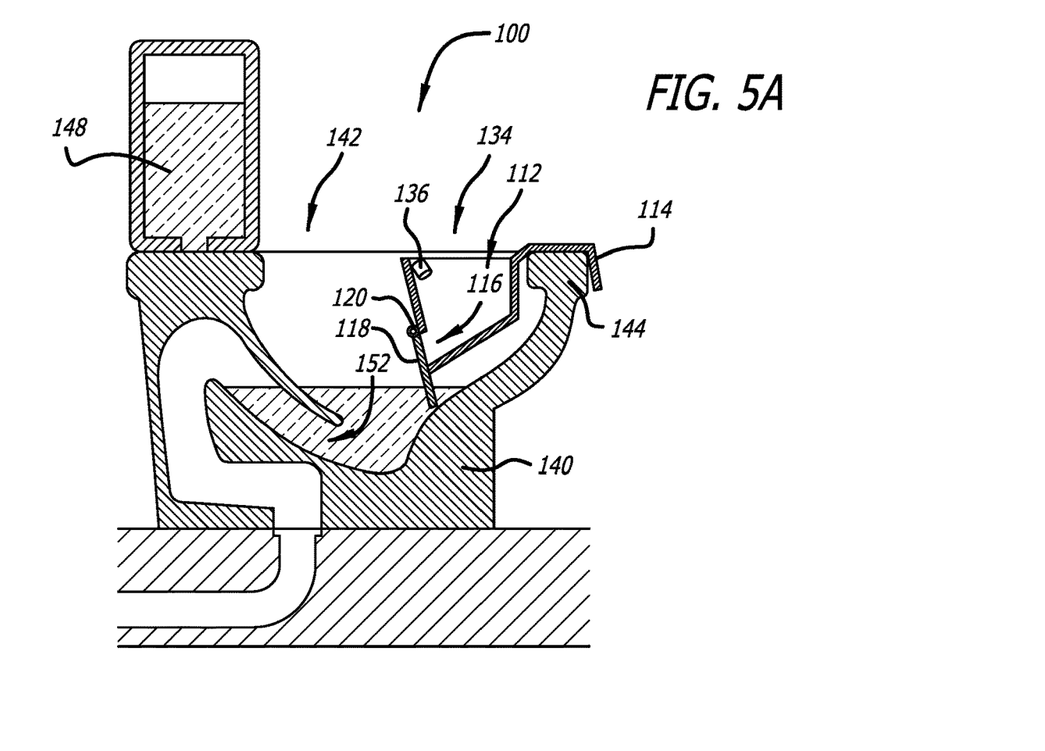
FIGS. 5A-5D illustrates a cross sectional side view of an exemplary method of measuring urine using the automated urinary output measuring system, in accordance with some embodiments.
Figure 5B:
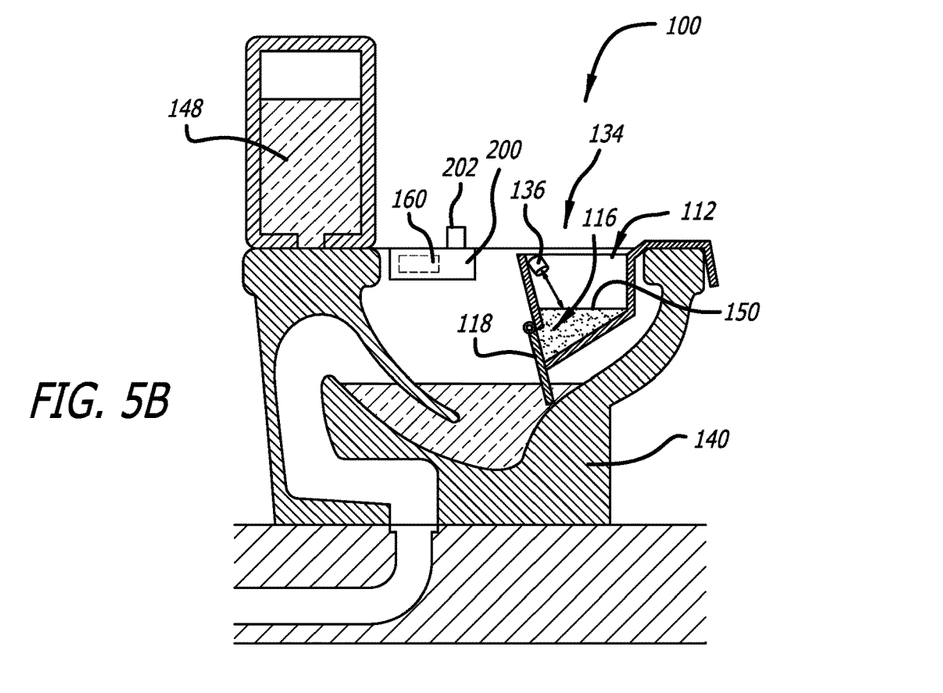

FIGS. 5A-5D illustrate a cross sectional side view of an exemplary method of measuring urinary output by using the automated urinary output measuring system 100, in accordance with some embodiments. In some embodiments, the automated urinary output measuring system 100 includes the automated urinary output measuring device 110 having the receiving trough 112 residing in the toilet 140, having the lip 114, the opening 116 and the door 118 coupled to the receiving trough 112 by the hinge 120. The door 118 may be configured in a closed orientation, wherein the door 118 seals the opening 116, preventing any portion of a volume of voided urine from passing therethrough. The device 110 includes the ultrasonic measuring system 134 including the one or more ultrasonic sensors 136 coupled to the console 160. The toilet 140 includes a tank 148 configured to hold a volume of flushing water and the bowl 142 having the rim 144 and an exit channel 152 configured to dispose of the content of the toilet bowl 142. The device 110 is configured to be secured to the rim 144 of the toilet 140 by the lip 114 and be suspended within the bowl 142 of the toilet 140. In some embodiments, the door 118 extends over the opening 116 creating the fluid tight seal, as illustrated in FIG. 5A. In some embodiments, the door 118 may contact the surface of the bowl 142. In some embodiments, as illustrated in FIG. 5B, the user may void a volume of urine into the receiving trough 112. In some embodiments, the door 118 is biased towards the closed configuration to maintain the volume of urine within the receiving trough 112. The ultrasonic measuring system 134 is activated by the console 160, or the user, using the one or more ultrasonic sensors 136 to measure the whole volume of voided urine within the receiving trough 112. As illustrated in FIG. 5B, the whole volume of voided urine within the trough 112 may be measured, using the one or more ultrasonic sensors 136. The one or more ultrasonic sensors 136 may generate one or more ultrasonic waves towards the air/urine interface 150 and measure the time of reflection of the ultrasonic waves from the air/urine interface 150 to the one or more ultrasonic sensors 136.

Figure 5C:
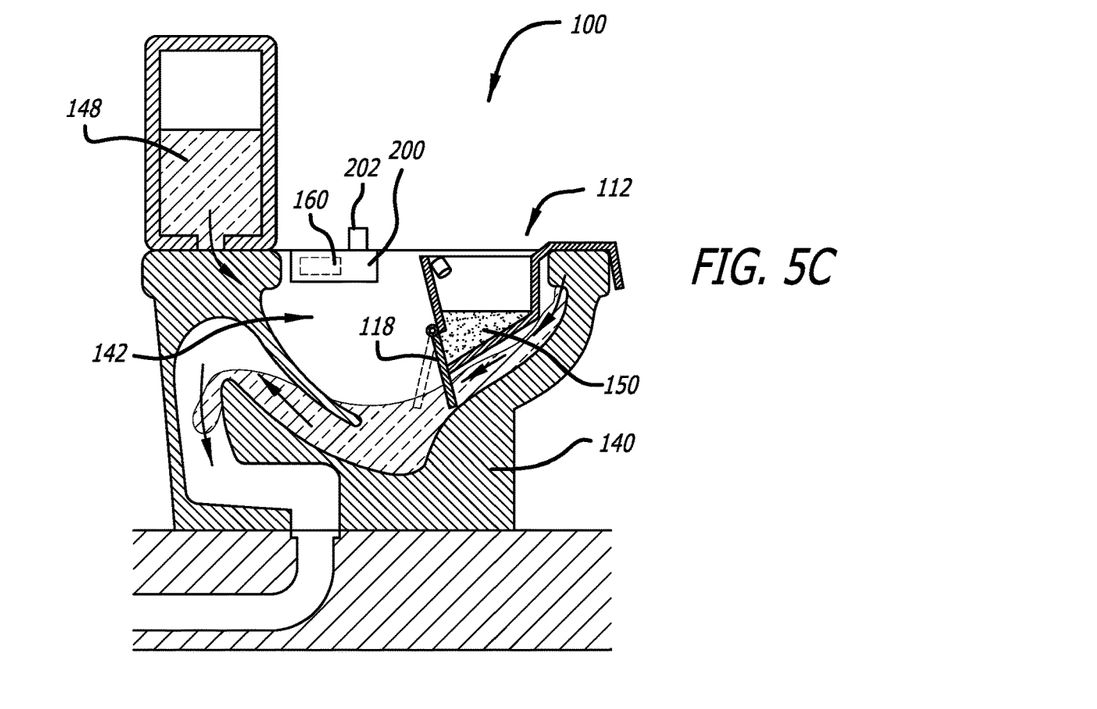
Figure 5D:
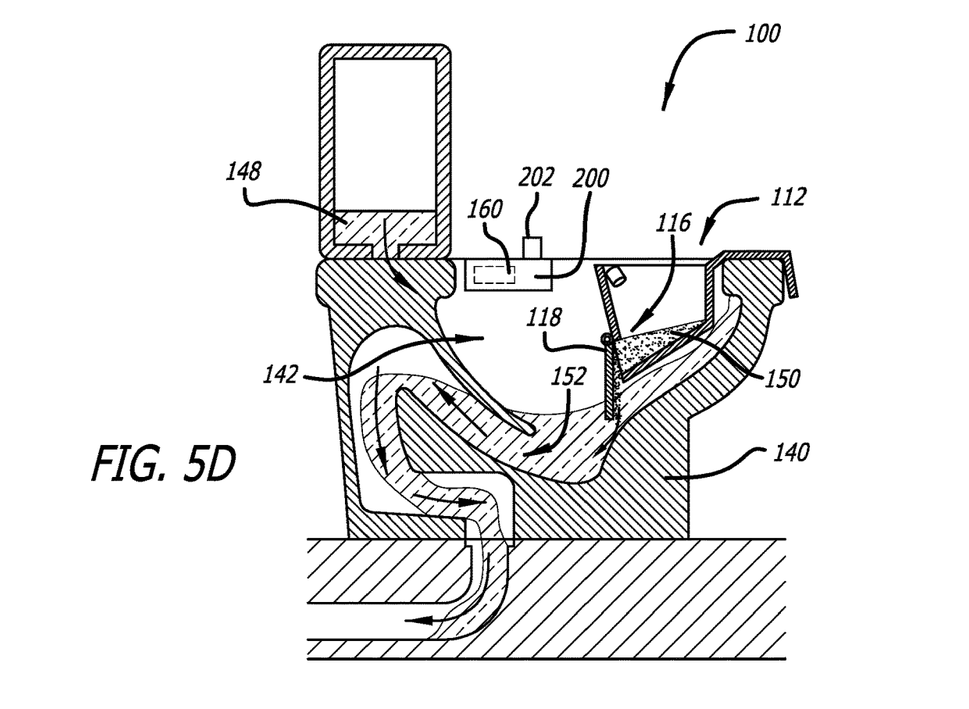

Once the whole volume of voided urine within the receiving trough 112 is measured, the toilet 140 may be activated to flush. The toilet 140 may be activated to flush by the button 202 of the flushing mechanism 200 and flush the toilet as appropriate to prevent overloading. In some embodiments, the ultrasonic measuring system 134 is activated by the button 202 of the flushing mechanism 200. The ultrasonic measuring system 134 may be activated to measure the whole volume of the voided urine in the receiving trough 112 right before flushing the toilet 140. As illustrated in FIG. 5C, the flushing of the toilet 140 released the volume of flushing water from the tank 148 into the bowl. A portion of the volume of flushing water released into bowl 142 may be configured to provide a pushing force on the door 118, transitioning the door 118 from the closed configuration to an opened configuration. The opened configuration occurs when the door 118 is moved from the opening 116 breaking the fluid tight seal, allowing any portion of the volume of voided urine to pass therethrough into the bowl 142 of the toilet 140. As illustrated in FIG. 5D, once the door 118 has been configured into the opened configuration, the whole volume of voided urine will be disposed of, draining out of the receiving trough 112 through the opening 116, into the bowl 142 to be disposed of through the exit channel 152. Once the whole volume of voided urine and the volume of flushing water have exited the bowl 142, the door 118 may be configured to be secured into the closed configuration. The console 160 may be configured to record the volume of voided urine and transmit the volume value and the time of day value to a computing device at any point after the whole volume of voided urine is measured. The console 160 may generate a notification to the computing device that the whole volume of voided urine has been disposed of. The receiving trough 112 may be removed from the toilet 140.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An automated urinary output measuring system comprising:
    an automated urinary output measuring device configured to be suspended from a rim of a sanitary hardware device and receive a volume of voided urine, the automated urinary output measuring device including:
        a receiving trough having an opening;
        a door coupled to the receiving trough by a hinge, the door configured to cover the opening, wherein:
            the door is configured to transition between an opened configuration and a closed configuration, and
            the door is configured to transition from the closed configuration to the opened configuration in response to a volume of flushing water from the sanitary hardware device, the volume of flushing water external to the receiving trough; and
        a lip extending from the receiving trough configured to detachably couple to the sanitary hardware device;
    an ultrasonic measuring system having a console coupled to one or more ultrasonic sensors, and
    a flushing mechanism configured to couple with the sanitary hardware device, having a button configured to activate flushing of the sanitary hardware device.

2. The automated urinary output measuring system according to claim 1, wherein the door is configured to transition from the closed configuration to the opened configuration as a result of user action.

3. The automated urinary output measuring system according to claim 1, wherein the console is configured to transition the door from the closed configuration to the opened configuration.

4. The automated urinary output measuring system according to claim 1, wherein the door extends past the opening to contact a surface of the sanitary hardware device.

5. The automated urinary output measuring system according to claim 1, wherein the flushing mechanism is in communication with the console.

6. The automated urinary output measuring system according to claim 1, wherein the console is coupled to the receiving trough.

7. The automated urinary output measuring system according to claim 1, wherein the console is located within the flushing mechanism.

8. The automated urinary output measuring system according to claim 1, wherein the sanitary hardware device includes a toilet.

9. The automated urinary output measuring system according to claim 8, wherein the receiving trough includes a front wall and a back wall, with the opening located at a bottom of the back wall and the lip extending from the front wall.

10. The automated urinary output measuring system according to claim 1, wherein the door is biased toward the closed configuration.

11. The automated urinary output measuring system according to claim 10, wherein in the closed configuration, the door creates a fluid tight seal over the opening.

12. The automated urinary output measuring system according to claim 1, wherein the console includes one or more processors, non-transitory computer readable medium, an energy source, and a plurality of logic modules.

13. The automated urinary output measuring system according to claim 12, wherein the plurality of logic modules, when executed by the one or more processors, are configured to perform operations including one or more of the following:
    activating the one or more ultrasonic sensors;
    receiving measured time of reflection values from the one or more ultrasonic sensors;
    determining the volume of urine within the receiving trough;
    correlating the measured time of reflection value with a volume value and a time of day value;
    configuring the door between the opened configuration and the closed configuration; and
    transmitting the volume value and the time of day value to a computing device.

* * * * *